US011578037B2

(12) United States Patent
Chen et al.

(10) Patent No.: US 11,578,037 B2
(45) Date of Patent: Feb. 14, 2023

(54) METHOD AND SYSTEM FOR PREPARING HIGH-PURITY TAURINE AND SALT

(71) Applicant: QIANJIANG YONGAN PHARMACEUTICAL CO., LTD., Qianjiang (CN)

(72) Inventors: Yong Chen, Qianjiang (CN); Xiquan Fang, Qianjiang (CN); Shaobo Li, Qianjiang (CN); Feng Liu, Qianjiang (CN)

(*) Notice: Subject to any disclaimer, the term of this patent is extended or adjusted under 35 U.S.C. 154(b) by 0 days.

(21) Appl. No.: 17/236,691

(22) Filed: Apr. 21, 2021

(65) Prior Publication Data

US 2021/0332008 A1     Oct. 28, 2021

(30) Foreign Application Priority Data

Apr. 22, 2020   (CN) .......................... 202010320728.8

(51) Int. Cl.
- *C07C 303/22* (2006.01)
- *C07C 303/44* (2006.01)
- *C07C 303/32* (2006.01)
- *B01J 39/18* (2017.01)

(52) U.S. Cl.
CPC ............ *C07C 303/22* (2013.01); *B01J 39/18* (2013.01); *C07C 303/32* (2013.01); *C07C 303/44* (2013.01)

(58) Field of Classification Search
None
See application file for complete search history.

(56) References Cited

U.S. PATENT DOCUMENTS

| 2,693,488 | A  | * | 11/1954 | Sexton .................. B01J 39/00 562/104 |
| 9,145,359 | B2 | * | 9/2015  | Hu ......................... C07C 303/24 |
| 10,071,955 | B1 | * | 9/2018  | Chen ..................... B01J 27/232 |
| 2013/0129332 | A1 |   | 5/2013  | Chen |
| 2015/0299113 | A1 |   | 10/2015 | Hu |
| 2015/0299114 | A1 |   | 10/2015 | Hu |

(Continued)

FOREIGN PATENT DOCUMENTS

| CN | 101486669 A | 7/2009 |
| CN | 101508657 A | 8/2009 |

(Continued)

OTHER PUBLICATIONS

Gunt (Thermal Process Engineering: Liquid-liquid extraction and solid-liquid extraction, downloaded from https://www.gunt.de/images/download/extraction_english.pdf on May 2, 2022) (Year: 2022).*

(Continued)

*Primary Examiner* — Amy C Bonaparte
(74) *Attorney, Agent, or Firm* — Porter Wright Morris & Arthur LLP

(57) ABSTRACT

A method for preparing high-purity taurine and salt by reacting ethylene oxide with bisulfite to generate isethionate, performing an ammonolysis reaction on the isethionate in combination with ammonia and a metal salt, evaporating the reaction solution and subjecting the concentrated solution to ion exchange to obtain an adsorption solution, extracting taurine from the adsorption solution, eluting adsorbed metal cations from the ion exchange system by an acid, and separately collecting the eluate containing a salt.

11 Claims, 6 Drawing Sheets

(56) References Cited

U.S. PATENT DOCUMENTS

2019/0029892 A1    1/2019   Chen
2021/0061758 A1    3/2021   Chen et al.

FOREIGN PATENT DOCUMENTS

| | | | |
|---|---|---|---|
| CN | 101508658 | A  | 8/2009 |
| CN | 101508659 | A  | 8/2009 |
| CN | 106699612 | B  | 8/2018 |
| CN | 109020839 | A  | 12/2018 |
| CN | 110483342 | A  | 11/2019 |
| CN | 110683970 | A  | 1/2020 |
| EP | 3786153   | A1 | 3/2021 |
| JP | 60-92253  | A  | 5/1985 |
| JP | 3-188057  | A  | 8/1991 |
| JP | 2013-535650 | A | 9/2013 |
| JP | 2017-533883 | A | 11/2017 |
| JP | 2019-25335 | A  | 2/2019 |

OTHER PUBLICATIONS

Barbera ("Sulfites, Thiosulfates, and Dithionates" Ullmann's Encyclopedia of Industrial Chemistry, 2000, p. 695-704, downloaded from https://doi.org/10.1002/14356007.a25_477 ) (Year: 2000).*

Lin Ruohui et al., Controlling the Size of Taurine Crystals in the Cooling Crystallization Process, Ind. Eng. Chem. Res., vol. 52, No. 37, pp. 13449-13458 (Aug. 12, 2013).

Official Action from corresponding Chinese Application No. 202010320728.8 dated Jan. 12, 2022, English Translation.

Official Action from corresponding Chinese Application No. 202010320728.8 dated Mar. 3, 2022, English Translation.

Official Action from corresponding Japanese Application No. 2020-218896 dated Jan. 27, 2022, English Translation.

Search Report from corresponding European Application No. 20210296.8 dated May 19, 2021, English Translation.

* cited by examiner

METHOD AND SYSTEM FOR PREPARING HIGH-PURITY TAURINE AND SALT

BACKGROUND

The present disclosure relates to a production method in a process for chemically synthesizing taurine, in particular to a method for producing high-purity taurine and salt (e.g., sodium sulfate or sodium chloride) by an ethylene oxide method, and a production system thereof.

Taurine (2-aminoethanesulfonic acid) is the most abundant sulfur-containing free amino acid in the body's cells. A chemical synthesis process route of taurine mainly includes an ethylene oxide method and an ethanolamine method, wherein preparation by the ethylene oxide method includes three steps:

(1) using ethylene oxide as a starting material, performing an addition reaction of ethylene oxide and sodium bisulfite to obtain sodium hydroxyethyl sulfonate (also known as sodium isethionate), wherein the main reaction is:

$$CH_2CH_2O+NaHSO_3 \rightarrow HOCH_2CH_2SO_3Na$$

(2) carrying out ammonolysis of the sodium hydroxyethyl sulfonate to obtain sodium taurate:

$$HOCH_2CH_2SO_3Na+NH_3 \rightarrow H_2NCH_2CH_2SO_3Na+H_2O$$

(3) adding sulfuric acid for acidification of the sodium taurate to obtain taurine and a salt:

$$2H_2NCH_2CH_2SO_3Na+H_2SO_4 \rightarrow 2H_2NCH_2CH_2SO_3H+Na_2SO_4$$

Chinese Patent Nos CN101508657, CN10158658, CN10158659 and CN101486669 describe a method of obtaining taurine and sodium sulfate by neutralizing sodium taurate with sulfuric acid. After cooling, by filtering a crystal suspension, a crude taurine product can be very easily obtained. However, the waste mother solution still contains taurine, ammonium sulfate and other organic impurities. These patents also provide feasible methods for further separating these components from the waste solution so as to implement economy of production and reduce discharge of wastes. However, since the materials are mixed together in the same mother solution, separation of the taurine, sulfate and the like is very difficult, the process design is complex, energy is simultaneously extracted, and cost of labor and the like is very high. Meanwhile, product purities of the taurine and the sulfate are relatively low.

U.S. Pat. No. 9,428,450B2 and U.S. Pat. No. 9,428,451B2 and European Patent No. EP3133060B1 describe cyclic methods for producing taurine, including a detailed description of a principle and method of separating the taurine from sodium sulfate. Solubility of the sodium sulfate is the maximum at a temperature of 33° C. At a temperature between 33° C. and 100° C., the solubility of the sodium sulfate is gradually and slightly reduced, but within a range of 0° C. to 33° C., the solubility of the sodium sulfate is sharply reduced. At a temperature of 40° C. or above, the sodium sulfate is separated out in the form of anhydrous crystals; and at a temperature of 30° C. or below, the sodium sulfate is separated out in the form of mirabilite (i.e., sodium sulfate decahydrate). Each time when the taurine is extracted, the temperature is controlled within a range of about 33° C., the taurine is extracted, and meanwhile, sulfate is prevented from being crystallized. The mother solution obtained after extraction is evaporated and crystallized, and the sodium sulfate is separated at a temperature of 70° C. to 95° C. The method mainly utilizes different solubility characteristics of the sulfate and the taurine at different temperatures to implement separation between the taurine and the sodium sulfate. The operation process is very complex. Since several materials are in the same mother solution system, purities of the products obtained by separation are necessarily relatively low.

CN110683970A describes a method for removing a sodium sulfate solid impurity from taurine. The method mainly is that the taurine is extracted from sodium sulfate using a deep-eutectic solvent preparation method. A deep-eutectic solvent is formed by utilizing monoethanolamine and the taurine, the sodium sulfate impurity is removed by filtering, and separation is carried out by utilizing a series of organic solvent reextraction and the like so as to obtain pure taurine. Such method introduces many types of organic solvents, and is also relatively cumbersome to operate; an intermediate control point needs to be very accurate, and the industrialization difficulty is very high.

CN109020839A describes a recycling process for preparing taurine by carrying out ammonolysis on sodium hydroxyethyl sulfonate. The content of a taurine crude product is 90%, sodium sulfate is transformed into a water glass product (sodium silicate) with low levels of impurities, and an effect of solving a problem of processing the sodium sulfate is achieved. The process has the main problem that the process does not solve the purity problem of the crude taurine product and the sodium sulfate and is just a subsequent processing process for low-content, low-purity products.

From the above, the existing process for preparing the taurine by a sulfuric acid neutralization method still has many defects in the aspect of separation and purification of the taurine and the sulfate, which are typically require a complex separation process, low purities of separated products, low extraction rates and high extraction costs. Therefore, a process capable of preparing high-purity taurine and sulfate or other salts is needed.

SUMMARY

The present disclosure aims to provide a method and system for preparing high-purity taurine and salt, which are simple in process and low in production cost.

The present disclosure provides a method for preparing high-purity taurine and salt that includes the following steps:
reacting ethylene oxide with bisulfite to generate isethionate;
carrying out an ammonolysis reaction on the isethionate and ammonia as well as a metal salt;
carrying out evaporation to obtain a concentrated taurine salt solution;
subjecting the concentrated solution to ion exchange in an ion exchange system to obtain an adsorption solution with a main ingredient of taurine;
separately collecting the adsorption solution, and extracting the taurine from the adsorption solution;
eluting adsorbed metal cations by an acid, and separately collecting the eluate; and
extracting the salt from the eluate or directly using the eluate as a salt solution product.

In one embodiment, the bisulfite is sodium bisulfite, ammonium bisulfite, potassium bisulfite or lithium bisulfite, particularly sodium bisulfite or ammonium bisulfite. Suitable metal salts include any one of, or a mixture of any two or more of, sodium hydroxide, potassium hydroxide, lithium hydroxide, sodium carbonate, potassium carbonate, lithium carbonate, sodium sulfate, potassium sulfate and lithium sulfate, particularly sodium hydroxide or sodium sulfate. Suitable acids include sulfuric acid, hydrochloric acid, phosphoric acid, water-soluble carboxylic acid, and sulfonic acid, particularly sulfuric acid or hydrochloric acid.

In one particular embodiment, the ion exchange system includes an adsorption unit and an elution unit, and each unit is respectively cleaned with purified water, and correspondingly obtained cleaning water is respectively collected.

In some embodiments, when the ion exchange system is operating in an adsorbing state, the adsorption solution is collected when pH of a solution at an outlet of the adsorption unit is 4 to 10. When operating in an eluting state, the eluate is collected when the pH of a solution at an outlet of the elution unit is 2 to 8.

Preferably, metal cations which are at least equivalent in molar amount to that of residual isethionate anions are allowed to enter the adsorption solution.

In terms of the taurine, the concentration of the concentrated solution (in terms of taurine) entering the ion exchange system is, for example, 10% to 35% (on a mass/volume basis, or % m/v).

The concentration of the acid added into the ion exchange system is, for example, 5% to 35% (on a mass/volume basis).

In particular embodiments, the adsorbent used in the ion exchange system is an ion exchange resin that adsorbs the cations (e.g., metal cations).

The step of extracting taurine from the adsorption solution can include, for example, the steps of: evaporation concentration, cooling crystallization and solid-liquid separation. Cooling crystallization and solid-liquid separation can be carried out at 5° C. to 30° C., and a taurine crude product obtained by separation has a taurine content of over 95% (g/g) and a taurine purity of 98.5% or above.

The salt (e.g., sodium sulfate) can be extracted from the eluate in an evaporation crystallization mode, wherein the evaporation crystallization is carried out at 60° C. to 125° C., and a salt crude product obtained by separation has a salt product content of over 97% and a salt product purity of 98.5% or above.

On the basis of the preparation method, the present disclosure further provides a system for producing high-purity taurine and salt, which can be used in a process for producing taurine by an ethylene oxide method. The system includes, for example, an addition reaction device, an ammonolysis reaction device, an evaporation device and a taurine salt concentrated solution collection device. By way of example, (a) a suitable addition reaction device can include a reaction kettle or reaction vessel, heat exchanger, transfer pump, storage tank, etc.; (b) a suitable ammonolysis reaction device can include an ammonolysis material and batching tank, heat exchanger, transfer pump, storage tank, high temperature and high pressure heater, high pressure pump, and high temperature and high pressure tower; (c) a suitable evaporation device can include a flash tank, heat exchanger, separator, transfer pump, storage tank, vacuum pump, etc.; and (d) a suitable taurine salt concentrated solution collection device can included a storage tank, mixer, transfer pump, etc. The size and form of this exemplary equipment can be designed and adjusted according to the applicable requirements and needs. The ammonolysis reaction device is provided with a metal salt inlet. The taurine salt concentrated solution collection device is connected with an ion exchange system for ion exchange. The ion exchange system is provided with an acid inlet, an adsorption solution outlet and an eluate outlet. The adsorption solution outlet is connected with a taurine extraction device (e.g., as described in ¶ [0062]), and the eluate outlet is connected with a salt extraction device (e.g., as described in ¶ [0062]). The ion exchange system is also provided with a purified water inlet, an adsorption unit cleaning water outlet and an elution unit cleaning water outlet. The cleaning water can be efficiently recycled. In some instances, the adsorption unit cleaning water outlet is connected with the taurine salt concentrated solution collection device, and the elution unit cleaning water outlet is connected with the salt extraction device.

Based on the above, the present disclosure relates to a method for producing high-purity taurine and salt. Materials of these two target products (taurine and salt) are efficiently separated in an ion exchange mode after the ammonolysis reaction. Strict separation of material systems is implemented, and moreover, extraction and purification are separately carried out, so that the two target products of the taurine and the salt have very good crystal forms of crystallization, a final extraction rate is greatly promoted, and the purities of the obtained taurine and salt are both very high, wherein the taurine crude product can reach the content of 95% or above and the purity of over 98.5%, the salt crude product can reach the content of 97% or above and can reach the purity of 98.5% or above, and, after recrystallization, the content of both the products is 99.5% or above.

In a conventional taurine production process, by taking a byproduct sulfate as an example, the taurine and the sulfate exist in the same mother solution system, separation has to be carried out by utilizing the solubility difference between the taurine and the sulfate, i.e., when solubility of sodium sulfate is the maximum, firstly, the taurine is extracted, and then a solution containing a great amount of taurine and sulfate after extraction is subjected to concentration separation; generally, firstly, the sulfate is separated out at a high temperature, then cooling is carried out to a temperature of about 33° C. to extract the taurine, and extraction is repeatedly carried out for many times. This process is very cumbersome to operate, and an extraction rate and product quality of the taurine are also seriously restricted. Obviously, all the materials exist in the same system and the materials are high in viscosity, resulting in a poor crystal form of crystallization of the sulfate, and thus, the sodium sulfate obtained by separation is relatively low in purity. Meanwhile, it is inevitable that the taurine crude product contains a great amount of sulfate, and it is also inevitable that the sulfate contains taurine, resulting in a difficulty of separating the taurine from the mother solution, and thus, the extracted taurine is relatively low in content and the yield is reduced.

Compared to the conventional production process, the preparation methods disclosed by the present disclosure are equivalent to extracting the taurine from the high-purity taurine mother solution system and extracting the salt from the high-purity salt mother solution system, and is completely not related to interference brought to product separation when two target products exist in the same maternal system, so that the processes for extracting two target products are simplified, the production cost is greatly reduced, and further, the automatic, intelligent and continuous design is also easier to implement in the whole product production process.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

Figure 1:
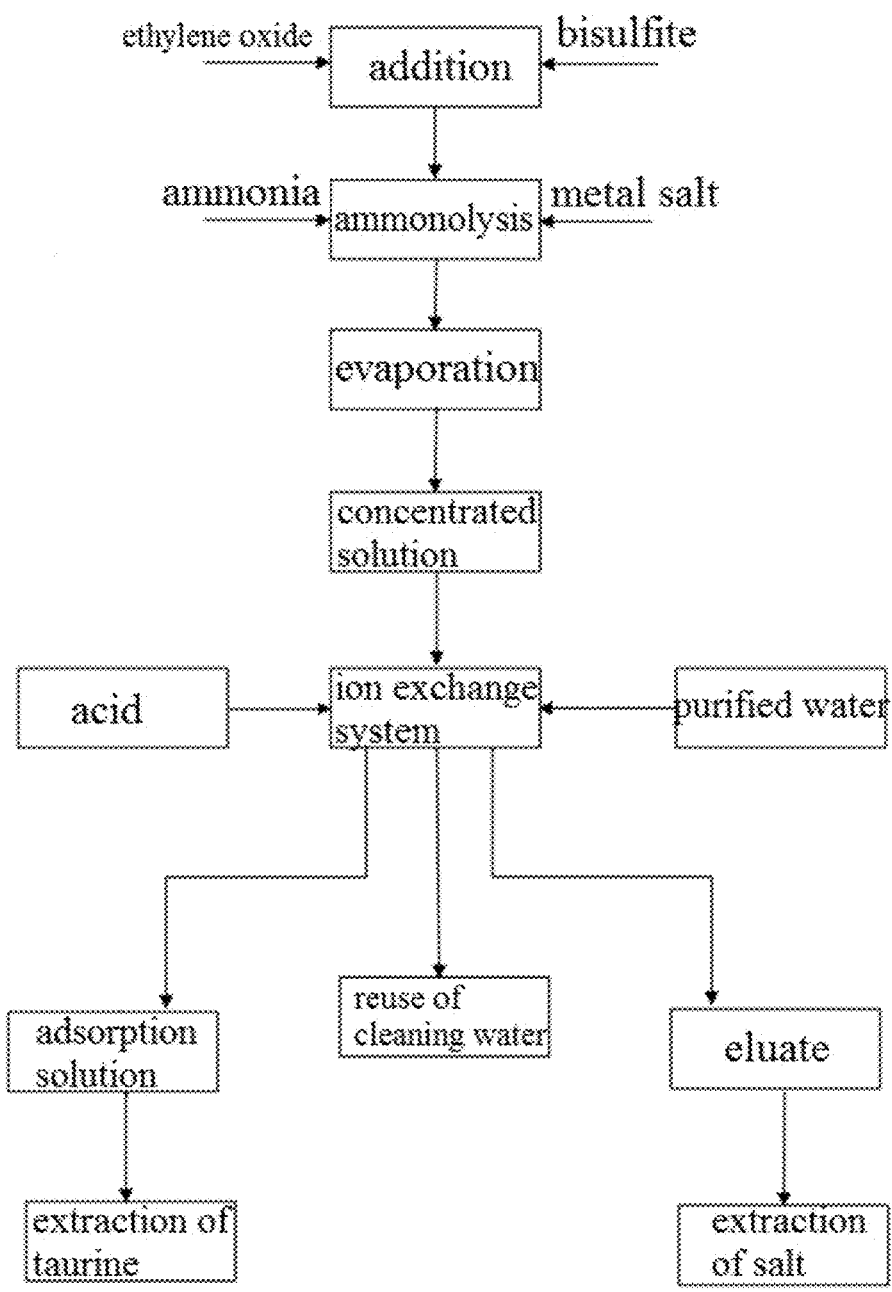
FIG. 1 is a flow chart of a process for preparing high-purity taurine and salt products in accordance with one embodiment of the present disclosure.
Figure 2:
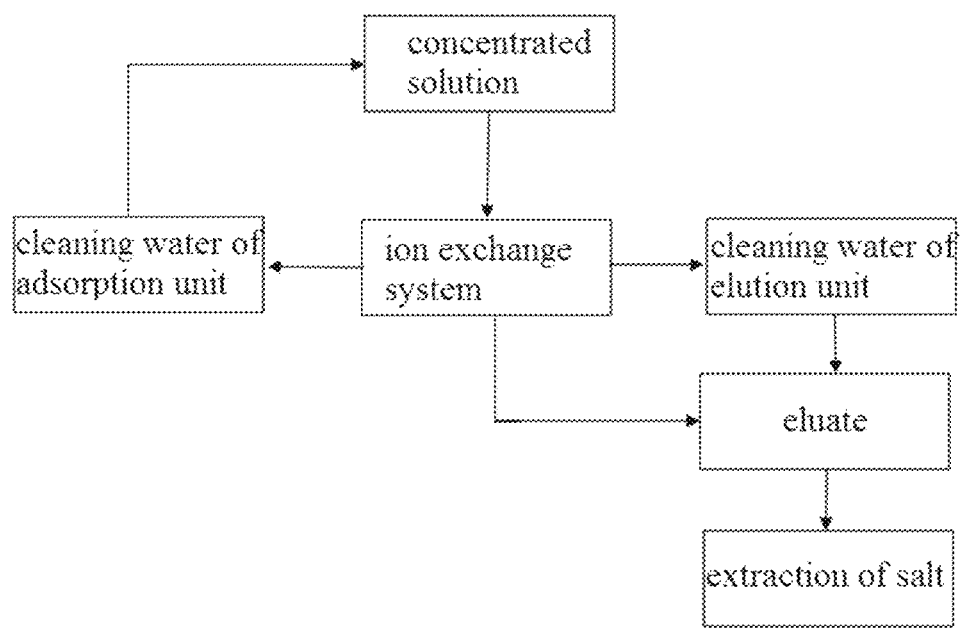
FIG. 2 is a flow chart of a process for recycling cleaning water of an ion exchange system in accordance with one embodiment of the present disclosure.
Figure 3:
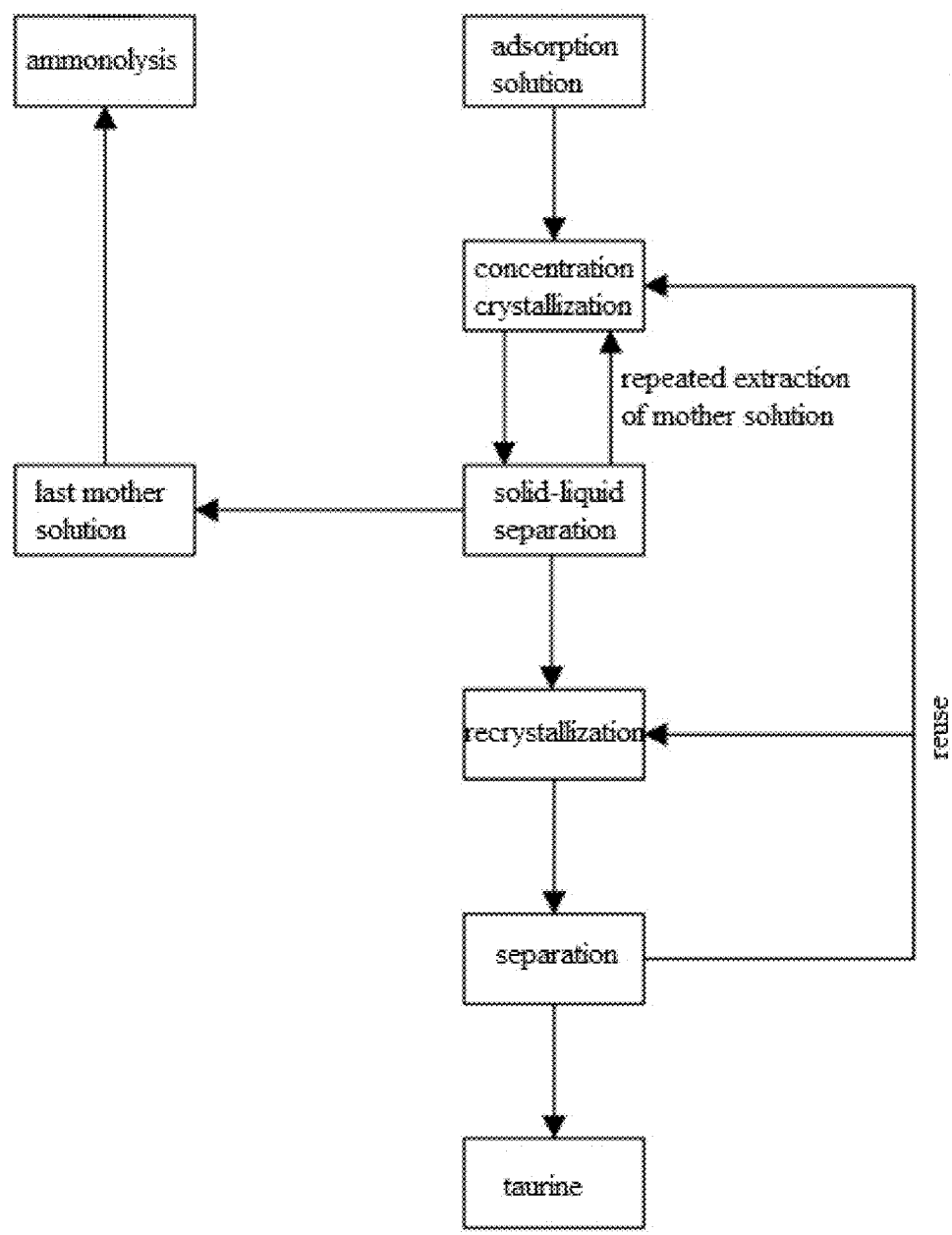
FIG. 3 is a flow chart of a process for extracting a taurine product from an adsorption solution in accordance with one embodiment of the present disclosure.
Figure 4:
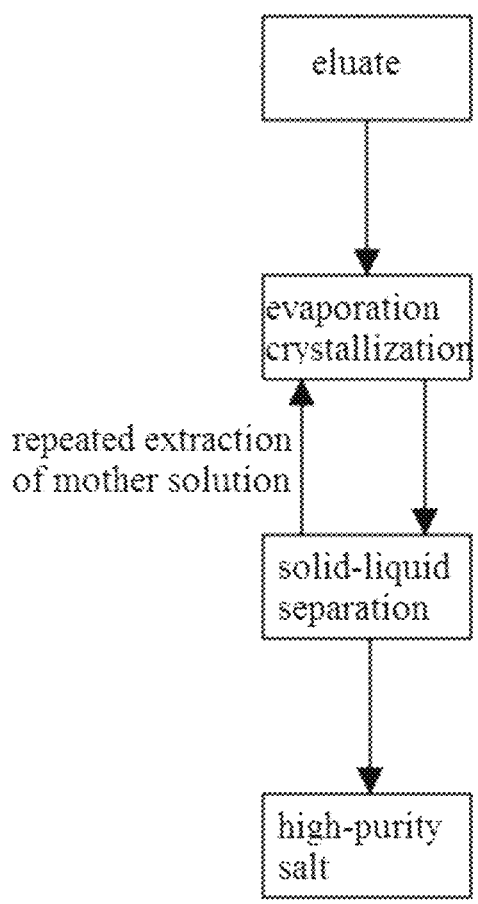
FIG. 4 is a flow chart of a process for extracting a sulfate product from an eluate in accordance with one embodiment of the present disclosure.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

With reference to FIGS. 1-4, a method for preparing taurine and salt includes the following steps S1 to S5:

S1: Ethylene oxide is reacted with a bisulfite solution to generate isethionate. In some embodiments, the process conditions are that: the concentration of the bisulfite solution is 25 wt % to 60 wt %, the molar ratio of bisulfite to ethylene oxide is (1.03 to 1.08):1, the reaction temperature is 50° C. to 80° C., and the pH of the reaction solution is 6 to 7.

S2: The isethionate solution obtained in the step S1 is mixed with ammonia (e.g., ammonia gas or ammonia water) and a metal salt to obtain a reaction solution. With respect to a mixing ratio, for 1 mol of isethionate, an amount of ammonia greater than 14 mol is added, and an amount of the metal salt is 0.01 mol to 1.3 mol (per mol of isethionate). After the ammonia is adsorbed until the ammonia content is greater than 20% g/ml (i.e., 20 g/100 ml), an ammonolysis reaction is performed. After the reaction is completed, residual ammonia gas is recycled as a raw material for the ammonolysis reaction. The reaction solution obtained after the ammonolysis reaction is completed is subjected to evaporation and concentration to obtain a concentrated solution of taurine salt.

In one embodiment, the ammonolysis reaction is carried out at 150° C. to 290° C., or 240° C. to 260° C., under a pressure of 10 MPa to 25 MPa for 15 to 60 min, or for 40 to 50 min.

If a last mother solution (also commonly referred to as the last mother liquor) is reused in the ammonolysis step, the amount of the metal salt added in S2 can be more, and if the last taurine mother solution is not reused, the amount of the metal salt can be reduced. For example, when the reaction solution in S2 is the isethionate, the ammonia and the metal salt, the molar ratio of isethionate:ammonia:metal salt can be 1:(14 to 17):(0.01 to 0.05); and when the reaction solution in S2 is the isethionate, the ammonia, the metal salt and the reused last mother solution, the molar ratio of isethionate: ammonia:metal salt can be 1:(14 to 17):(0.05 to 0.3). When the isethionate is ammonium isethionate is in use, an additional amount of the metal salt should be used, such that the molar ratio of the ammonium isethionate to the ammonia to the metal salt can be 1:(14 to 17):(1.01 to 1.3).

Following evaporation and concentration of the reaction solution in S2, the concentrated sodium taurate solution obtained in step S2 has a concentration of 10% to 35% m/v (in terms of taurine), or a concentration of 10% to 25%. A solution added in the preparation process may be purified water or reused cleaning water discharged from an adsorption unit of an ion exchange system.

S4: The concentrated taurine salt solution is then subjected to adsorption in an ion exchange system such that the taurine salt is converted into taurine, followed by water cleaning, elution and water cleaning treatment of the ion exchange system. An adsorbent of the ion exchange system preferably is resin, particularly a resin with a function that cations can be adsorbed. Suitable resins include cation exchange resins, such as cation exchange resins having a carboxylic group, a sulfonic group, a phosphate group, a phenolic group and similar materials. Alternatively, a chelating resin with the function of adsorbing cations can also be used. The resin exchanges H+ for the metal cations in the taurine salt (e.g., sodium if the taurine salt is sodium taurate), with the resin adsorbing the metal cations and converting the taurine salt into taurine.

Metal ions are adsorbed by the resin and, after adsorption, when the pH of a solution at an outlet of the adsorption unit is 4 to 10, the adsorption solution (containing primarily taurine) is collected. In the adsorbing process, part of the cations are allowed to penetrate through, i.e., metal cations which are at least equivalent in amount (on a molar basis) to the isethionate anions present in the concentrated taurine salt solution are allowed to penetrate through the resin to enter the adsorption solution. The content of the metal cations in the collected adsorption solution can be 0.05% to 2% m/v, or 0.1% to 1%. Unreacted isethionate will remain in the concentrated taurine salt solution, and the ion exchange system only adsorbs the cations (all of the anions penetrate through). It is better to allow the metal ions which are equivalent in amount to the isethionate anions to penetrate through so as to ensure that ingredients at an adsorption solution outlet are the taurine and the isethionate. Otherwise, adsorbing excessive or all the metal ions will result in the ingredients at the adsorption solution outlet to exist in a form of the taurine and isethionic acid. Isethionic acid in the ingredients is relatively unstable and is liable to deteriorate and decompose in the subsequent heating, evaporating, concentrating process. Isethionic acid is also relatively high in viscosity, which significantly influence subsequent extraction of the taurine. In addition, isethionic acid is a medium strong acid, and under superacid conditions, a crystalline state of the taurine is poor, adversely affecting subsequent extraction of the taurine and reduction of the purity of the taurine.

Purified water is added into the ion exchange system for cleaning following adsorption. A use volume of the purified water generally is one to two times the volume of a resin column of the ion exchange system, and the adsorption unit is cleaned. The cleaning water is collected. Cleaning can be carried out until taurine cannot be detected in the collected cleaning water. The collected cleaning water can be reused in the concentrated solution after the ammonolysis reaction.

Next, an acid used as an eluting agent is added into the ion exchange system, and the metal ions which have been adsorbed in the resin are continuously eluted. The acid may be sulfuric acid, hydrochloric acid, phosphoric acid, water-soluble carboxylic acid, sulfonic acid and the like. The concentration of the acid added to the ion exchange system for elution is 5% to 35% m/v, or 15% to 25%. Only the cations are adsorbed in the ion exchange system, and thus, the eluted metal ions are relatively high in purity, thereby ensuring that a salt solution with a very high purity is collected. Specifically, if the acid is the sulfuric acid, the correspondingly obtained salt is sulfate, if the acid is the hydrochloric acid, the correspondingly obtained salt is chloride, and the sulfate and the chloride have high solubility in the water. The eluate can be collected when the pH of the solution at an outlet of the elution unit is 2 to 8.

The elution unit is cleaned by the purified water. A use volume of the purified water generally is one to two times the volume of the resin column of the ion exchange system. The cleaning water obtained after water cleaning is collected and is reused in the salt extraction process.

A cleaning mode can be adopted for both the adsorption and elution units, and the cleaning processes can be implemented by adopting an automatic control system to carry out online operation, so that complete isolation between adsorption and elution can be implemented, thereby ensuring complete isolation between a taurine solution in the adsorption solution and the salt solution in the eluate. The cleaning water can be recycled into corresponding material systems according to ingredients of included materials.

A principle of ion exchange to which the present disclosure relates is illustrated as follows. In the ion exchange system, by utilizing the property that the ion exchange resin only adsorbs the cations, the ion exchange resin is used for adsorbing the metal cations in a material (i.e., the concentrated taurine salt solution entering the ion exchange system). In the adsorbing process, H+ is exchanged into the material so as to implement separation of the metal cations in the material and convert the taurine salt into taurine. After adsorption is completed, by water cleaning, it is guaranteed that there is no residual adsorption solution material in the ion exchange resin (e.g., taurine); and the obtained cleaning water can be reused in a production process system. The resin after cleaning contains a great amount of metal cations, and does not contain other components. The metal cations in the resin are then eluted by the acid, the resin is recycled into an acid state, and a corresponding aqueous solution of the metal salt is collected. After elution is ended, residual acid and salt are removed up by water cleaning. After the ion exchange process is carried out, the aim of independently separating the taurine and the salt in two material systems is finally fulfilled so as to respectively carry out purification on the taurine and the salt. In comparison, in the original conventional process, the taurine and the salt are mixed and the two products are extracted in the same material system.

Illustration will be further carried out in detail below by taking a process of carrying out ammonolysis to generate sodium taurate and generating the sodium sulfate after adding the sulfuric acid as an example.

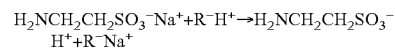

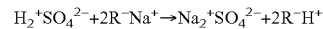

After the ammonolysis reaction is performed on a reaction solution obtained after sodium hydroxyethyl sulfonate (sodium isethionate), sodium hydroxide (a metal salt) and ammonia liquor are mixed, a main ingredient in the reaction solution is sodium taurate. The reaction solution also contains excess sodium hydroxide, a small amount of sodium hydroxyethyl sulfonate which is not completely reacted, sodium taurate derivatives and the like. When the ammonolysis reaction is completed and the ammonia is recycled, in the ion exchange system, a flow rate and pH are controlled so as to enable sodium ions to be adsorbed according to a certain proportion. Meanwhile, it has to be ensured that a portion of residual sodium ions penetrate through in the adsorption solution, so that the main ingredients of the collected adsorption solution are the taurine and the sodium hydroxyethyl sulfonate (sodium isethionate). The sodium hydroxyethyl sulfonate is very high in solubility, and due to very low content of the sodium hydroxyethyl sulfonate in the system, the sodium hydroxyethyl sulfonate cannot be separated out, so that an extraction rate of the taurine will not have the problem caused by influence of separation-out of the sodium sulfate in the conventional process. Furthermore, due to the high solubility of the sodium hydroxyethyl sulfonate, when solid-liquid separation is carried out, a little residual sodium hydroxyethyl sulfonate on the surface of the taurine can be very easily washed off in a water cleaning mode, and thus, the purity of the taurine product is also correspondingly improved. Thus it can be seen that according to the present disclosure, the method implements complete separation between a taurine solution system and a sodium sulfate solution system by the ion exchange system, is an efficient and simple separation method, and meanwhile, also fulfills the aim of preparing the high-purity taurine and sodium sulfate.

S4: the adsorption solution collected in step S3 is separately collected, and extraction of the taurine is carried out. In the extraction process, the collected adsorption solution can be subjected to evaporation concentration, cooling crystallization and solid-liquid separation by adopting methods of the prior art. In one implementation, the content of the adsorption solution for evaporation concentration is 25% to 40% m/v (in terms of the taurine), the cooling crystallization is carried out at 5° C. to 30° C., the solid-liquid separation is carried out at 5° C. to 30° C., or 15° C. to 20° C., a crude taurine product and a mother solution are obtained. The crude taurine product has a content of over 95% taurine with a purity of 98.5% or above. The mother solution can be repeatedly concentrated and crystallized to extract the taurine so as to further improve the extraction rate. Main ingredients of the mother solution in the taurine extraction system are the taurine and the isethionic acid metal salt. The last mother solution can be recycled as a raw material directly or after impurity removal treatment. For example, the last mother solution can be returned into the step S2 to participate in the ammonolysis reaction. In one particular embodiment, water and activated carbon are added to the obtained crude taurine product to be subjected to recrystallization, and after solid-liquid separation, a finished product taurine with a higher purity is obtained. In order to better carry out recycling, the mother solution after recrystallization purification can be returned to the initial stage of carrying out evaporation concentration on the adsorption solution in the step S4, and then concentration crystallization and separation are carried out.

According to a specific implementation implementation of the crude taurine product recrystallization process, the crude taurine product is dissolved with 2 to 3 times of purified water, activated carbon of which the mass is 0.1% to 0.3% of total mass of the crude product is added, decoloration is carried out for 15 min to 40 min at a temperature of 85° C. to 98° C., and after the activated carbon is filtered, the filtrate is cooled to a temperature of 5° C. to 30° C. or 10° C. to 20° C. for crystallization. Then, the crystallized material is dried after being separated so as to obtain the high-purity finished taurine.

S5: the material of the eluate collected in step S3 is allowed to enter the extraction treatment process for the salt, and any one the methods of the prior art can be adopted for this purpose. In one embodiment, the salt is directly extracted using an evaporation crystallization process, and then solid-liquid separation is carried out. The crystallization can be carried out at 60° C. to 125° C., or 85° C. to 110° C. After the eluate is crystallized, solid-liquid separation can be carried out at 60° C. to 100° C., or 85° C. to 95° C., and the sulfate (salt) obtained by separation has a sulfate content of over 97% and a purity of 98.5% or above. In order to further improve the purity of the salt, the obtained salt also can be recrystallized.

The method for producing the high-purity taurine and salt provided by the present disclosure can be carried out in a discontinuous, semi-continuous or continuous mode.

Figure 5:
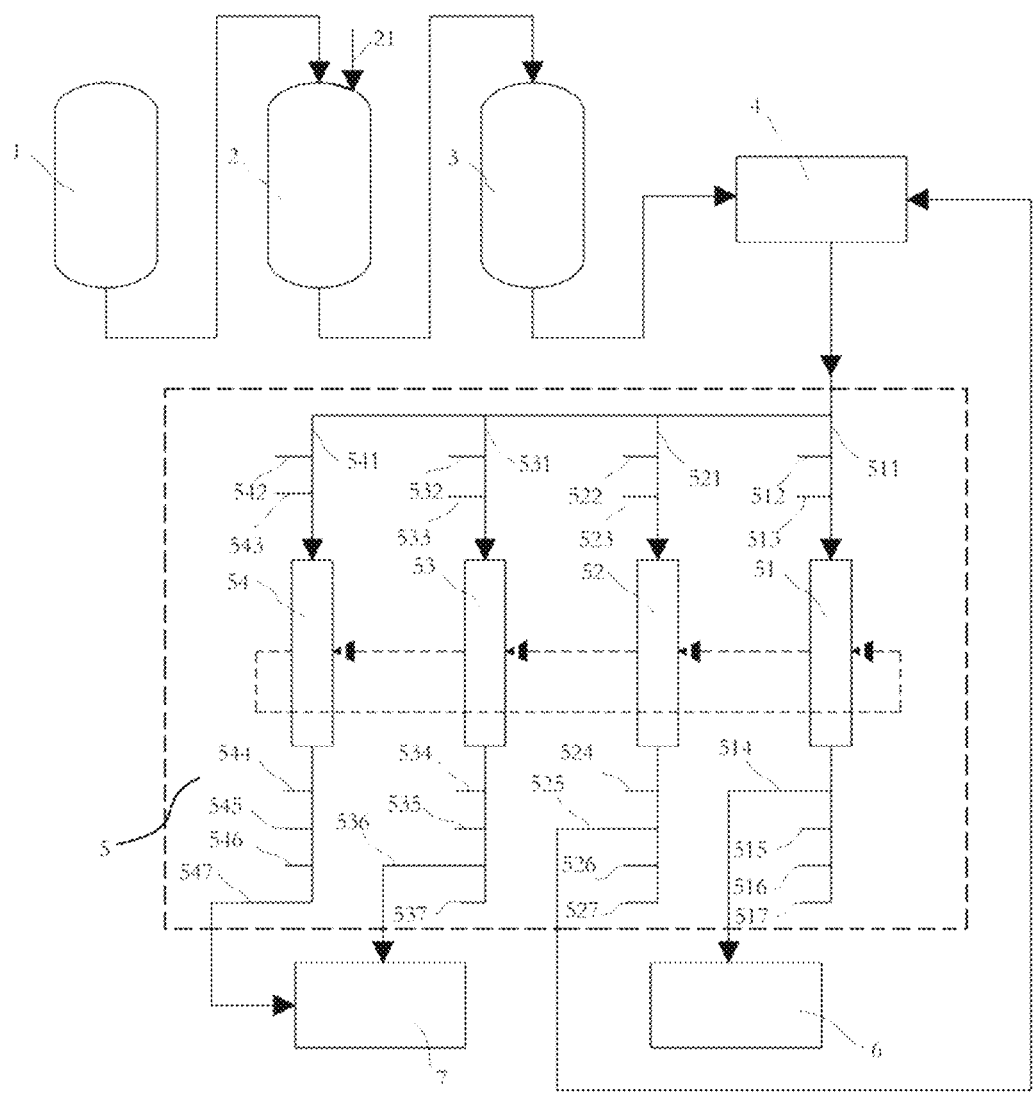
FIG. 5 is a schematic diagram of a production system for preparing high-purity taurine and salt products in accordance with one embodiment of the present disclosure.
Figure 6:
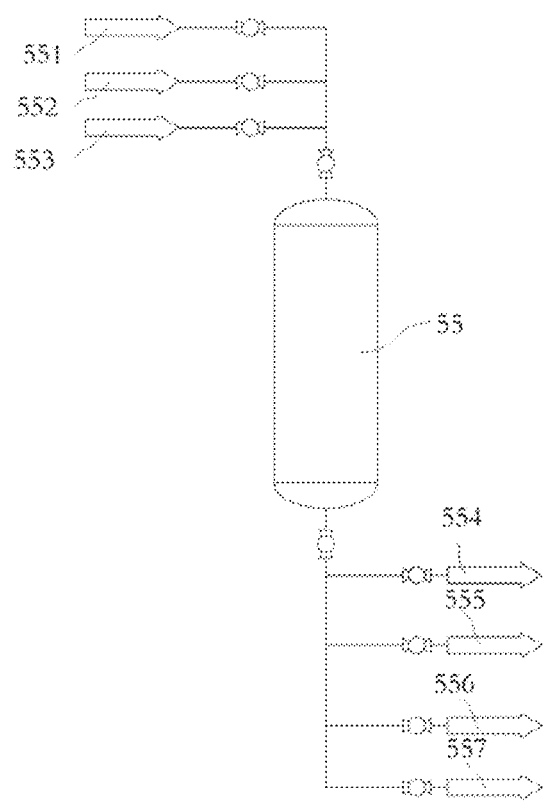
FIG. 6 is a structural schematic diagram of single resin column in accordance with one embodiment of the present disclosure.

Certainly, as an option, the eluate collected in the step S3 can also be directly used as a high-purity sulfate (salt) solution.

the present disclosure also provides a production system for carrying about the above-described process for preparing the high-purity taurine and salt. As shown in FIG. 5 and FIG. 6, the production system includes an addition reaction device 1 for reacting the ethylene oxide and the bisulfate, an ammonolysis reaction device 2, an evaporation device 3 (for concentrating the taurine salt solution following ammonolysis) and a taurine salt concentrated solution collection device 4. The taurine salt concentrated solution collection device 4 is connected with an ion exchange system 5, such that a concentrated taurine salt solution can be supplied to the ion exchange system 5 to be subjected to ion exchange. Each device and system above are all provided with material inlets and outlets and control valves, which are required for process demands, wherein the ammonolysis reaction device 2 is provided, for example, with a material inlet 21 for supplying the metal salt, an ammonia liquor and reused ammonia gas inlet (not shown in FIG. 5) and an inlet for receiving material discharged by the addition reaction device 1.

The present disclosure can employ any existing ion exchange system, and the structure of the ion exchange system is not limited. For example, the ion exchange system may be a fixed bed, or may also be a pulse bed or a simulated moving bed which combines a continuous countercurrent system technology on the basis of a conventional fixed bed resin adsorption and ion exchange process, or may be a continuous exchange bed. An existing continuous exchange bed includes a plurality of resin columns, and can complete the whole technological processes of adsorption, elution and water cleaning in one process cycle. In comparison, the fixed bed carries out operations of all the steps in an intermittent process in a mode that each step is carried out separately for a period of time.

In the specific embodiment shown in FIG. 5, the ion exchange system 5 includes four cation adsorption resin columns 51, 52, 53 and 54, and an electromagnetic pump (not shown). Each resin column is provided with three material inlets and four material outlets, and entrance and exit of the materials are controlled by valves. The three material inlets include concentrated solution inlets 511, 521, 531 and 541, acid inlets 512, 522, 532 and 542, and purified water inlets 513, 523, 533 and 543. The material outlets include adsorption solution outlets 514, 524, 534 and 544, adsorption cleaning water outlets 515, 525, 535 and 545, eluate outlets 516, 526, 536 and 546, and elution cleaning water outlets 517, 527, 537 and 547. The adsorption solution outlets 514, 524, 534 and 544 are connected with a taurine extraction device 6, and the eluate outlets 516, 526, 536 and 546 are connected with a salt extraction device 7. The adsorption cleaning water outlets 515, 525, 535 and 545 are connected with the concentrated solution collection device 4, and the elution cleaning water outlets 517, 527, 537 and 547 are connected with the salt extraction device 7. The material inlets and the material outlets of the resin columns are all fixed. Thus, the three material inlets for each column can share one inlet to the column, the four material outlets for each column can share one outlet from the column, and entrance and exit switching of each material is implemented, for example, by a valve array or in any one of other feasible valve control modes. When the ion exchange system comprising multiple (e.g, four) columns, the system operates, in any given time period the four resin columns are operating in different process states, thereby simulating a continuous ion exchange system operational mode.

FIG. 5 depicts the working states of four resin columns 51, 52, 53 and 54 in the same time period, in which processes of adsorption, water cleaning, elution and water cleaning are sequentially carried out. Specifically, the resin column 51 is in an adsorbing state, the valve of the concentrated solution inlet 511 is opened, the concentrated solution in the concentration solution collection device 4 flows into the resin column 51, the valves of the acid inlet 512 and the purified water inlet 513 are closed, at a material outlet end, the valve of the adsorption solution outlet 514 is opened, the taurine extraction device 6 collects the adsorption solution, and the valves of the adsorption cleaning water outlet 515, the eluate outlet 516 and the elution cleaning water outlet 517 are closed. The resin column 52 is in a water cleaning state, the valve of the purified water inlet 523 is opened, purified water is introduced into the resin column 52, the valves of the concentrated solution inlet 521 and the acid inlet 522 are closed, at the material outlet end, the valve of the adsorption cleaning water outlet 525 is opened, cleaning water flows into the concentrated solution collection device 4, and the valves of the adsorption solution outlet 524, the eluate outlet 526 and the elution cleaning water outlet 517 are closed. The resin column 53 is in an eluting state, the valve of the acid inlet 532 is opened, acid is introduced into the resin column 53, the valves of the purified water inlet 533 and the concentrated solution inlet 531 are closed, at the material outlet end, the eluate outlet 536 is opened, the eluate flows into the salt extraction device 7, and the valves of the elution cleaning water outlet 537, the adsorption solution outlet 534 and the adsorption cleaning water outlet 535 are closed. The resin column 54 is in a water cleaning state, the valve of the purified water inlet 543 is opened, the purified water is introduced into the resin column 54, the valves of the concentrated solution inlet 541 and the acid inlet 542 are closed, at the material outlet end, the valve of the elution cleaning water outlet 547 is opened, elution cleaning water flows into the salt extraction device 7, and the valves of the adsorption solution outlet 544, the eluate outlet 546 and the adsorption cleaning water outlet 545 are closed. Besides the equipment above, the system further includes a control system, power equipment, connecting parts, pipeline valves and the like which are necessary for production, all of which are common technical means in the art and are not repeated herein. In the processes of adsorption, elution and twice water washing of the ion exchange system, separate collection of an adsorption unit and an elution unit on outlet materials can be implemented by the valve array control system, and the outlet materials include the adsorption solution, the eluate and the cleaning water discharged from the adsorption unit and the elution unit.

The pH values of the outlet solutions are acquired by pH value monitoring devices (e.g., pH meters) arranged in the outlet of the adsorption unit and the outlet of the elution unit in the ion exchange system, and discharge time of the adsorption solution and the eluate are selected so as to collect an aqueous solution containing a high-purity taurine adsorption solution material and the high-purity salt.

The taurine extraction device (or system) 6 and the salt extraction device (or system) 7 can include any applicable equipment and systems known to those skilled in the art for carrying out evaporation, cooling crystallization (or crystallization), and solid-liquid separation. For example, conventional evaporation equipment, cooling crystallization equipment/crystallization equipment and solid-liquid separation equipment can be utilized as the extraction device (i.e., extraction system). The solid-liquid separation equipment in the extraction device can include any applicable equipment known to those skilled in the art for such use, such as a panel centrifuge, a top-suspended centrifuge, a continuous horizontal spiral centrifuge, a plate-and-frame filter press and the like.

As shown in the alternative embodiment of FIG. 6, if only one resin column 55 is included in the ion exchange system, the system similarly includes three material inlets 551, 552 and 553 and four material outlets 554, 555, 556 and 557, the three material inlets can share one inlet of the column 55, the four material outlets can share one outlet of the column 55, the ion exchange system is controlled by the valves to sequentially proceed to different working states of adsorption, water cleaning, elution and water cleaning in an intermittent operating mode.

In order to illustrate the technical effects of the preparation method disclosed by the present disclosure, the following examples are used for illustration. Unless otherwise specified, raw materials used in the following embodiments are all commercially available products. Unless otherwise specified, the individual steps used in the following embodiments are all conventional steps; and unless otherwise specified, the material content all refers to percentage by mass volume.

Example 1

This example shows a preparation process of an ammonolysis solution.

Preparation of sodium hydroxyethyl sulfonate (sodium isethionate): sodium bisulfite and ethylene oxide are mixed according to a molar ratio of the sodium bisulfite to the ethylene oxide of 1.05:1, and the mixture is subjected to a reaction under the conditions of a pH value of 6.2 to 6.8 and a temperature of 60° C. to 65° C. so as to obtain sodium hydroxyethyl sulfonate.

Preparation of ammonolysis solution: the sodium hydroxyethyl sulfonate, sodium hydroxide (i.e., a metal salt) and ammonia are subjected to a reaction for 45 min under the conditions of a temperature of 255° C. and a pressure of 10 MPa to 18 MPa. After the reaction is completed, ammonia gas is discharged and recycled, and concentration is carried out to obtain a concentrated ammonolysis reaction solution (i.e., a concentrated sodium taurate solution).

Example 2

This example shows that the ion exchange system adsorbs the sodium ions from the sodium taurate in the concentrated ammonolysis reaction solution and implements separation in two material solution systems for the taurine and the sodium sulfate (salt).

The concentrated ammonolysis solution is prepared into an 18 L of solution in which the taurine content of the solution is 20% (m/v). 12 L of sulfuric acid solution with a concentration of 15% m/v is prepared. In a small-sized ion exchange system having a resin adapted for sodium ion adsorption, the prepared taurine solution is pumped into the system. The pH of the collected adsorption solution is controlled within a range of 7 to 8 (by controlling the amount of the taurine solution), the content of the sodium ions in the adsorption solution is 0.05% to 1% m/v, 22 L of adsorption solution is collected in total, the taurine content is 16%, and the sodium hydroxyethyl sulfonate (sodium isethionate) content is 1.5%. The system is then cleaned with purified water, and the cleaning water is collected and reused in the concentrated ammonolysis solution, and cleaning is carried out until taurine cannot be detected in the collected cleaning water leaving the ion exchange system. Next, the sulfuric acid solution with a concentration of 15% is pumped into the cleaned ion exchange system. The pH of the collected eluate is controlled within a range of about 3 to 5 (by controlling the amount of sulfuric acid), and 16 L of eluate of which the sodium sulfate content is 17% is collected in total. After eluate collection is completed, the ion exchange system is once again cleaned with purified water, and the cleaning water is discharged from the ion exchange system, so that a cyclic adsorbing and separating function can be achieved. The system can implement continuous feeding and discharging control, for example, by adopting a plurality of resin columns, thereby ensuring stability of the material content of the different collected solutions.

| Items | Adsorption Solution | Eluate |
| --- | --- | --- |
| Taurine Content (g/ml) | 16% | less than 1 ppb |
| Sodium Hydroxyethyl Sulfonate Content (g/ml) | 1.50% | less than 1 ppb |
| Sodium Sulfate Content (g/ml) | smaller than 10 ppm | 17% |

Example 3

This embodiment shows a process (e.g., FIG. 2 and FIG. 3) of respectively carrying out concentration extraction on the adsorption solution and the eluate which are collected in Example 2.

(1) Extraction of the adsorption solution: 3 L of adsorption solution is taken and concentrated to a taurine concentration of 33%, and cooling is carried out to a temperature of 15° C. to carry out centrifugal separation so as to obtain a crude taurine product with a taurine content of 95.5% (g/g) and moisture content of 3.5% (g/g). When moisture is removed, the taurine content is 98.96% (g/g), and the purity is very high. After the taurine is extracted, in the mother solution, the taurine content is 10%, the sodium hydroxyethyl sulfonate content is 4.7%, and the sulfate content is less than 10 ppm.

(2) Extraction of the eluate: 3 L of eluate is taken, subjected to six-time concentration crystallization at a high temperature of 95° C. and subjected to centrifugal separation to obtain sodium sulfate (salt) with a sodium sulfate content of 97.5% (g/g) and a moisture content of 2.0% (g/g). After the moisture is removed, the sodium sulfate content is 99.49% (g/g), and the purity is very high. In the mother solution, the taurine content is less than 1 ppb, the sodium hydroxyethyl sulfonate content is less than 1 ppb, and the sulfate content is 35%.

|  | Extraction of Taurine from Adsorption Solution | Extraction of Sodium Sulfate from Eluate |
|---|---|---|
| Taurine Content (g/g) | 95.50% | <1 ppb |
| Sodium Hydroxyethyl Sulfonate Content (g/g) | <0.05% | <1 ppb |
| Sodium Sulfate Content (g/g) | <10 ppm | 97.50% |
| Moisture Content (g/g) | 3.50% | 2.00% |
| Purity After Removal of Moisture | 98.96% | 99.49% |

|  | Mother Solution after Extraction of Taurine | Mother Solution after Extraction of Sodium Sulfate |
|---|---|---|
| Taurine Content (g/ml) | 10% | <1 ppb |
| Sodium Hydroxyethyl Sulfonate Content (g/ml) | 4.70% | <1 ppb |
| Sodium Sulfate Content (g/ml) | <10 ppm | 35% |

Example 4

This example shows a process of respectively carrying out recrystallization on the taurine and the sodium sulfate.

Recrystallization of the taurine: 200 g of the crude taurine product collected in Example 3 is taken, 500 g of purified water is added, 0.4 g of activated carbon is added. The mixture is heated to a temperature of 95° C., and the temperature is maintained for 20 min. Thereafter the activated carbon is removed by filtration, cooling is carried out to a temperature of 15° C. to carry out crystallization, the crystallization solution is separated, and after drying, 155 g of dry fine taurine product is obtained. The fine mother solution obtained by separation can be recycled and reused in the previous process which may be the concentration crystallization process, or can be returned into a next batch of materials in the recrystallization process. Detected data is as follows:

| Items | High-Purity Fine Product Taurine |
|---|---|
| Appearance: | white crystal particles, no odor and tartish taste |
| Content($C_2H_7NSO_3$): | 99.9% |
| Chloride PPM: | <10 ppm |
| Sulfate PPM: | <10 ppm |
| Ammonium Salt PPM: | <10 ppm |
| Residues on Ignition: | 0.005% |
| Loss on Drying: | 0.05% |
| Heavy Metal (in terms of Pb): | <1 ppm |
| Arsenic Salt (in terms of As): | <1 ppm |

Recrystallization of the sodium sulfate: 200 g of sodium sulfate collected in Example 3 is taken, 500 g of purified water is added, heating is carried out to a temperature of 95° C. to carry out evaporation crystallization, the crystallization solution is separated, and after drying, 190 g of dry fine sodium sulfate (salt) is obtained. The mother solution obtained by separation can be recycled and reused in the previous process, i.e., the concentration crystallization process, or can be returned into a next batch of materials in the recrystallization process.

Detected data is as follows:

| Items | High-Purity Fine Product Sodium Sulfate |
|---|---|
| Appearance: | white crystal particles |
| Content($Na_2SO_4$): | 99.90% |
| Chloride PPM: | <10 ppm |
| Moisture Content | 0.02% |
| Heavy Metal (in terms of Pb): | <1 ppm |
| Arsenic Salt (in terms of As): | <1 ppm |

Example 5 (Prior Art)

This example shows a conventional method for producing and separating the taurine and the sodium sulfate.

Extraction of the taurine: after the ammonolysis concentrated solution is prepared into a certain concentration, under the stirring condition, concentrated sulfuric acid is slowly added for neutralization, a temperature in the neutralizing process is controlled within a range of 50° C. to 60° C., when pH is 8.0, the addition of the acid is stopped, cooling is carried out to a temperature of 33° C. to carry out crystallization, and separation is carried out to obtain a crude taurine product and a mother solution. In the crude product, the taurine content is 90% (g/g), the sodium sulfate content is 3% (g/g) and the moisture content is 6%. In the mother solution, the taurine content is 15%, and the sulfate content is 25%.

Extraction of the sodium sulfate: the mother solution obtained after the taurine is extracted is concentrated again to a concentration of 33% sodium sulfate, the sodium sulfate is separated at a high temperature of 95° C. or above, and in the product obtained by separation, the sodium sulfate content is 90% (g/g), the moisture content is 5%, and the taurine content in the sulfate is 4%. The mother solution subjected to separation is cooled to a temperature of 33° C. to extract the taurine, and separation and extraction of the sodium sulfate and the taurine are repeatedly carried out in this way.

|  | Extraction of Taurine by Conventional Process | Extraction of Sodium sulfate by Conventional Process |
| --- | --- | --- |
| Taurine Content (g/g) | 90.00% | 4% |
| Sodium Hydroxyethyl Sulfonate Content (g/g) | <0.05% | <0.1% |
| Sodium Sulfate Content(g/g) | 3% | 90.00% |
| Moisture Content (g/g) | 6% | 5.00% |
| Purity After Removal of Moisture | 95.74% | 94.74% |

Example 6

This example shows that the ion exchange system adsorbs the sodium ions and implements separation into two material solution systems of the taurine and the salt (in this instance, sodium chloride).

A concentrated ammonolysis solution is prepared into 18 L of solution in which the taurine content is 20%. 24 L of hydrochloric acid solution with a concentration of 12% is prepared. The prepared taurine solution is pumped into the ion exchange system. The pH of the collected adsorption solution is controlled within a range of 7 to 8, the content of the sodium ions in the adsorption solution is 0.05% to 1%, 22 L of adsorption solution is collected in total, the taurine content is 16%, and the sodium hydroxyethyl sulfonate content is 1.5%. The system is cleaned with purified water, the cleaning water is collected and reused in a material of the concentrated ammonolysis solution, and cleaning is carried out until taurine cannot be detected in the collected cleaning water. Next, the hydrochloric acid solution with a concentration of 12% is pumped into the cleaned system. The pH of the collected eluate is controlled within a range of about 3 to 5, and 28 L of eluate of which the sodium chloride content is 17% is collected in total. After collection is completed, the system is cleaned with the purified water.

| Items | Adsorption Solution | Eluate |
| --- | --- | --- |
| Taurine Content (g/ml) | 16% | <1 ppb |
| Sodium Hydroxyethyl Sulfonate Content(g/ml) | 1.50% | <1 ppb |
| Sodium Chloride Content (g/ml) | <10 PPm | 17% |

By the embodiments above, it can be obviously seen that in the conventional process, the taurine and the sodium sulfate of the material systems are mixed together, resulting in that the product content of the extracted and separated taurine and sodium sulfate is relatively low, the moisture content is high, the purities are poor, and meanwhile, the process of process control is relatively complex. Preparation according to the method disclosed by the present disclosure essentially solves the problem of a case that the taurine and sodium sulfate/sodium chloride material systems are mixed together to be subjected to extraction and separation, and fulfills the aim of preparing the high-purity taurine and sodium sulfate/sodium chloride.

Finally, it should be noted that the embodiments above are merely used for illustrating the technical solutions of the present disclosure, but not intended to limit the present disclosure. Although the present disclosure has been illustrated in detail with reference to the above-mentioned embodiments, those of ordinary skill in the art will understand that they still can make modifications to the technical solutions described in the above-mentioned embodiments, or replace preparation reaction conditions, or make equivalent replacements to part of the technical characteristics, and those modifications or replacements will not enable the essences of the corresponding technical solutions to depart from the spirit and scope of the technical solutions of the embodiments of the present disclosure.

While various embodiments of the present disclosure have been described in detail above, it will be understood that the components, features and configurations, as well as the methods of manufacturing the devices and methods described herein are not limited to the specific embodiments described herein.

What is claimed is:

1. A method for preparing high-purity taurine and a salt, comprising the steps of:
    (a) reacting ethylene oxide with a bisulfite to generate an isethionate;
    (b) carrying out an ammonolysis reaction on the isethionate generated in step (a) in combination with ammonia and a metal salt to obtain a taurine salt solution;
    (c) concentrating the taurine salt solution to obtain a concentrated taurine salt solution;
    (d) subjecting the concentrated taurine salt solution to ion exchange in an ion exchange system to obtain an adsorption solution having a main ingredient of taurine, and, when the pH of a solution at an outlet of the ion exchange system is 4 to 10, separately collecting the adsorption solution;
    (e) extracting the taurine from the adsorption solution; and
    (f) eluting adsorbed metal cations from the ion exchange system by an acid, and, when the pH of a solution at an outlet of the ion exchange system is 2 to 8, separately collecting the eluate containing a salt;
    wherein metal cations which are at least equivalent in molar amount to residual isethionate anions are allowed to enter the adsorption solution.

2. The method according to claim 1, further comprising the step of extracting the salt from the eluate.

3. The method according to claim 1, further comprising the steps of:
    after step (d) and before step (f), cleaning the ion exchange system with water and thereafter collecting the water as adsorption cleaning water; and
    after step (f), cleaning the ion exchange system with water and thereafter collecting the water as elution cleaning water.

4. The method according to claim 1, wherein in terms of the taurine, the concentration of the concentrated solution entering the ion exchange system is 10% to 35%.

5. The method according to claim 4, wherein the bisulfite comprises sodium bisulfite, ammonium bisulfite, potassium bisulfite or lithium bisulfite.

6. The method according to claim 5, wherein the metal salt in step (b) is any one of, or a mixture of any two or more of, sodium hydroxide, potassium hydroxide, lithium hydroxide, sodium carbonate, potassium carbonate, lithium carbonate, sodium sulfate, potassium sulfate and lithium sulfate.

7. The method according to claim 6, wherein the acid in step (f) comprises sulfuric acid, hydrochloric acid, phosphoric acid, a water-soluble carboxylic acid or sulfonic acid.

8. The method according to claim 7, wherein the acid in step (f) is added into the ion exchange system as a solution having an acid concentration of 5% to 35%.

9. The method according to claim 1, wherein an adsorbent of the ion exchange system is an ion exchange resin; the ion exchange resin having a function that the cations of the taurine salt are adsorbed by the resin and exchanged with H+ ions to generate taurine from the taurine salt.

10. The method according to claim 9, wherein the step of extracting taurine from the adsorption solution comprises the steps of: evaporation concentration, cooling crystallization and solid-liquid separation, the cooling crystallization and solid-liquid separation are carried out at 5° C. to 30° C., and a crude taurine product obtained by the solid-liquid separation has a taurine content of over 95% and a purity of 98.5% or above.

11. The method according to claim 10, further comprising the step of extracting the salt from the eluate, wherein the salt is extracted from the eluate in an evaporation crystallization process, wherein the evaporation crystallization is carried out at 60° C. to 125° C., and a crude salt product obtained by separation has a salt content of over 97% and a purity of 98.5% or above.

\* \* \* \* \*